United States Patent [19]

Prichard

[11] 4,146,741
[45] Mar. 27, 1979

[54] CONVERSION OF FURAN TO 1,4-BUTANEDIOL AND TETRAHYDROFURAN

[75] Inventor: William W. Prichard, Hockessin, Del.

[73] Assignee: E. I. Du Pont de Nemours and Company, Wilmington, Del.

[21] Appl. No.: 824,841

[22] Filed: Aug. 15, 1977

[51] Int. Cl.$^2$ ............................................. C07C 31/18
[52] U.S. Cl. ............................... 568/865; 260/346.11
[58] Field of Search ..................... 568/865; 260/635 E

[56] References Cited

U.S. PATENT DOCUMENTS

| | | | |
|---|---|---|---|
| 2,440,929 | 5/1948 | Bremner et al. | 260/635 E |
| 2,546,019 | 3/1951 | Smith | 260/635 E |
| 2,700,685 | 10/1955 | Cooper et al. | 260/635 E |

FOREIGN PATENT DOCUMENTS 114928  1958  U.S.S.R.

OTHER PUBLICATIONS

Watson, "Ind. Eng. Chem. Prod. Res. Develop.," vol. 12, No. 4, 1973, pp. 310, 311.

*Primary Examiner*—Joseph E. Evans

[57] ABSTRACT

Furan is hydrogenated in the presence of a nickel catalyst and a dicarboxylic acid having 4 to 10 carbons to produce 1,4-butanediol and tetrahydrofuran.

13 Claims, No Drawings

CONVERSION OF FURAN TO 1,4-BUTANEDIOL AND TETRAHYDROFURAN

BACKGROUND OF THE INVENTION

1. Field of the Invention

Furan is hydrogenated in an aqueous system in the presence of a nickel catalyst and a dicarboxylic acid having 4 to 10 carbons to produce 1,4-butanediol and tetrahydrofuran.

2. Prior Art

Furan has been hydrogenated in a neutral or weakly acid aqueous system in the presence of a nickel catalyst as shown by Russian Pat. No. 114,928 (1958) to P. A. Moshkin et al. to produce 1,4-butanediol, tetrahydrofuran and small amounts of butanol. One example shows the inclusion of a small amount of formic acid in the reaction mixture. James A. Watson, Ind. Eng. Chem. Prod. Res. Develop. 12 (4) 310–311 (1973) shows the same general reaction where acetic acid is present in the reaction mixture. In both processes the yield of 1,4-butanediol is not as high as could be desired and unwanted by-products are produced, such as the mono- and diformate, and mono- and diacetate esters of 1,4-butanediol. These esters have boiling points quite close to the boiling point of 1,4-butanediol itself and it is expensive and difficult to distill them off; in fact the diacetate ester of 1,4-butanediol has the same boiling point as 1,4-butanediol and cannot be separated by distillation. Accordingly the 1,4-butanediol produced by these processes contains the said esters as impurities. Pure, "polymer grade" 1,4-butanediol is necessary in the manufacture of useful high molecular weight polyesters from terephthalic acid, for example, and accordingly the impure diol produced by the above-mentioned prior art processes cannot be used directly. The present invention yields polymer grade 1,4-butanediol directly by the simple expedient of avoiding the formation of the undesired esters.

STATEMENT OF THE INVENTION

The invention is the process of making 1,4-butanediol and tetrahydrofuran by contacting furan, water and hydrogen at a temperature in the range of 150°–195° C. under a hydrogen pressure of 500–900 pounds per square inch (psi) in the presence of a nonpyrophoric nickel hydrogenation catalyst and an aliphatic dicarboxylic acid or anhydride of 4 to 10 carbon atoms or a derivative thereof having one free carboxylic group, the water/furan molar ratio being at least 1 and the amount of said dicarboxylic acid or derivative being at least 0.25 equivalent of COOH per liter of the combined volume of water and furan.

By operating in this way the products of the reaction are tetrahydrofuran (THF), water, polymer grade 1,4-butanediol, butanol and a low molecular weight polyester of 1,4-butanediol and aliphatic dicarboxylic acid which is nondistillable at 120° C. at 10 mm. Distillation at 100° C. removes the water, tetrahydrofuran and butanol; raising the distillation temperature to 120° C. at 10 mm pressure then separates out the polymer grade 1,4-butanediol and leaves the low molecular weight polyester in the distillation pot. This residue polyester is acidic in nature and can be used as the source of the aliphatic dicarboxylic acid (by hyrolysis) in subsequent runs. By changing the amounts of dicarboxylic acid, water and furan, the ratio of 1,4-butanediol to tetrahydrofuran can be varied.

Aliphatic dicarboxylic acids or their anhydrides containing 4 to 10 carbons include succinic, maleic, fumaric, α-methylsuccinic, α,α'-dimethylsuccinic, glutaric, α- and β-methylglutaric, α- and β-ethylglutaric, adipic, pimelic, suberic and sebacic. Preferred are the acids having 4 to 6 carbons, as succinic, maleic, fumaric, glutaric and adipic. A derivative of the acid having one free carboxylic group includes the mono-alkali metal salt, the mono ester of a primary alcohol, the mono ester of a diol and the like. Examples are monosodiumadipate, monoethyladipate, mono(4-hydroxybutyl)adipate and the like. Use of the di-alkali metal salt results in nearly complete conversion of the furan to tetrahydrofuran and neutral to basic conditions do not give 1,4-butanediol.

The concentration of the dicarboxylic acid component should be at least 0.25 equivalents of —COOH groups per liter of total furan and water and may be much higher. Little change in the THF/1,4-butanediol ratio results from acid concentration of greater than 1.75 equivalents per liter.

A small part of the formed 1,4-butanediol is converted to the nonvolatile distillation residue which can be recycled since it can act as a source of the dicarboxylic acid component.

The hydrogen pressure of the reaction can vary from 500–900 psi but it is preferred to use 600–800 psi for purposes of efficient operation.

The time for reaction is generally 3–12 hours, but is dependent upon catalyst and temperature, etc. The reaction can be carried out as a batch or continuous process.

The molar ratio of water to furan should be at least 1:1 if appreciable diol is to be obtained, and may be much higher, e.g., up to 10:1 or more. Little advantage results from the use of ratios higher than 3.5:1.

The nickel hydrogenation catalyst can be any reduced and stabilized nickel hydrogenation catalyst as is known in the art. Preferred are catalysts containing both nickel and copper if a high ratio of diol is desired in the product. The copper content can range from about 2 to about 35% by weight of the amount of nickel. Suitable supports are silica, alumina, titania, silicon carbide, kieselguhr and carbon. The nickel concentration on the support may be varied widely, from 1 to 60% nickel. The amount of catalyst used may be varied to increase or decrease the reaction time. In general, catalysts for this reaction are available commercially.

With the preferred catalysts, the reaction is generally carried out in the range of 155°–185° C. and 600–800 psi $H_2$ for optimum diol yields. Higher temperatures and higher $H_2$ pressures, both of which accelerate the reduction, result in higher ratios of tetrahydrofuran to 1,4-butanediol in the product. Much lower temperatures and pressures, while operable, substantially increase the reaction time, rendering the process uneconomical.

The temperature, pressure, and catalyst are interrelated variables. With the more active hydrogenation catalysts the reaction rate may be reduced by lowering the temperature or $H_2$ pressure with a resulting increase in the ratio of 1,4-butanediol to tetrahydrofuran in the product.

If a highly active hydrogenation catalyst is employed at relatively high temperatures and pressures, the reduction to THF becomes so rapid that little or no diol is formed. Similarly, if the acidity of the system is too low or the water concentration is insufficient, the amount of tetrahydrofuran is increased at the expense of the diol.

To maximize the ratio of 1,4-butanediol to tetrahydrofuran formed in the reaction, three conditions are needed. First, the mole ratio of water to furan should be at least 2.5. Second, the COOH concentration of the acidic component in the system should be at least 1.6 equivalents per liter. Third, the hydrogenation catalyst must be nonpyrophoric. Particularly preferred are supported nickel catalysts which have been reduced with hydrogen and then stabilized by controlled exposure to air so that they are no longer pyrophoric.

While the exact mechanism of the ring opening of furan to yield 1,4-butanediol is not known, hydrogenation to give a dihydrofuran may be the first step. This can be followed by a second hydrogenation to yield THF or by a hydrolytic ring opening to give a hydroxy aldehyde, which is then reduced to the butanediol, as follows:

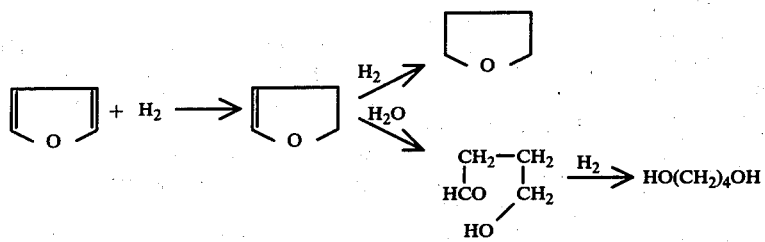

SPECIFIC EMBODIMENTS OF THE INVENTION

The following are illustrative examples in which all parts are by weight and all temperatures are Centigrade unless specified otherwise. Yields are based on the amount of furan charged. The percentages and ratios are on a molar basis.

EXAMPLE 1

A. A 100 ml pressure vessel, lined with "Hastelloy C" was charged with 23 g furan, 20 g water, 2.4 g adipic acid, and 1 g of a catalyst containing by weight about 47.2% Ni, 16.6% Cu, 2.38% Cr, 6.56% Al and oxygen available as Girdler T 1350 RS. The sealed vessel was cooled, evacuated and pressured with 100 psi hydrogen. The vessel was then heated to 180°, the pressure raised to 750 psi with $H_2$ and shaken vigorously for 11.5 hrs at which time the reaction was complete since no more hydrogen was consumed. The vessel was then cooled, vented, and the contents discharged. The liquid product weighed 45.7 g. A known quantity (9.58 g) of dimethylformamide was added as an internal standard and the solution assayed by gas-liquid chromatography. A 1.5' × ⅛" "Porapak" Q packed column was used with a thermal conductivity detector. The temperature of the column was programmed upward from 100° by 20°/min to 200° at 20 ml helium flow per minute. Factors for conversion of area percent to mole percent were determined by measurement of known mixtures of furan, tetrahydrofuran, 1,4-butanediol and dimethylformamide. The analysis showed a yield of 37.4% tetrahydrofuran, 51.7% of 1,4-butanediol, and 1% n-butanol. A Ni content of 9 ppm was determined by a colorimetric technique using dimethyl glyoxime.

After filtration to remove the solid particles of catalyst, the liquid reaction mixture was subjected to distillation. Water, tetrahydrofuran, butanol and dimethylformamide were distilled off after which the distillation was carried out at 128°/10 mm to recover 1,4-butanediol. A semisolid residue of about 3.3 g remained in the distillation apparatus. This residue was a low molecular weight polyester of butanediol with adipic acid.

B. To contrast part A above with the prior art, the above process was repeated with the exception that the adipic acid was replaced by 2 g of acetic acid. The reaction was complete in 4.5 hours. Analysis showed the reaction product contained 35.2% tetrahydrofuran, 55.3% of 1,4-butanediol, 0.9% butanol and 3.2% butanediol acetates. These acetates have about the same volatility as the diol; for example 1,4-butanediol diacetate has a boiling point of about 230° which is the same as that of 1,4-butanediol and could not be separated from the diol by distillation

EXAMPLE 2

A pressure vessel was charged as in Example 1, except the adipic acid was replaced by the 3.3 g of the distillation residue of Example 1. A heating period of 7 hrs at 185° and 800 psi $H_2$ was used. The product weighed 45.06 g and assayed for 1.3% recovered furan, 38.55% tetrahydrofuran (THF), 55.35% 1,4-butanediol (BAD) and 1.4% n-butanol. The nonvolatile residue weighed 2.83 g.

The following table lists examples using the general procedure of Example 1 except the adipic acid was replaced by the nonvolatile residue from the preceding examples. It is to be noted that no increase occurred in the amount of the nonvolatile residue. It is believed that some hydrolysis of the residue occurs to yield a dicarboxylic acid.

| Ex. | Nonvol.Residue | g | Hrs | % THF | % 1,4-BAD |
|-----|----------------|------|-----|-------|-----------|
| 3   | Ex Example 2   | 2.83 | 7.5 | 41.6  | 52.7      |
| 4   | Ex Example 3   | 2.23 | 7.0 | 43.6  | 54.5      |
| 5   | Ex Example 4   | 1.45 | 7.0 | 45.8  | 51.4      |

EXAMPLE 6

The vessel and charge of Example 1 were used with the adipic acid being replaced by 2.17 g of glutaric acid. The reduction was carried out at 180° and 800 psi $H_2$ for 7.5 hrs. The product recovered weighed 45.48 g. A weighed amount of 1,5-pentamethylene glycol was added as an internal standard and the solution assayed using a "Porapak" P column (⅛" × 2½') at 180° with a He flow of 20 ml/min. Known standard mixtures of water, THF, 1,4-BAD and 1,5-pentamethylene glycol were prepared and assayed to calibrate the analysis. The yield of THF was 48.4% and of 1,4-BAD 51.7%.

EXAMPLE 7

The process of Example 6 was repeated using 1.95 g of succinic acid in place of the glutaric acid and with 20 g furan, 10 g water and 10 g dioxane, the dioxane being added for subsequent glc analysis. The reaction mixture was held at 185° and 800 psi $H_2$ for 3½ hrs. The mole ratio of THF to 1,4-BAD in the product was 1.03, and the yield of THF was 45.8% and of 1.4-BAD 45.5%. Distillation of the product left 2.27 g nonvolatile residue.

EXAMPLE 8

The charge of Example 1 was used, replacing the Ni-Cu-Cr catalyst with 1.0 g of a Ni-on-$Al_2O_3$ catalyst containing 25% Ni (Harshaw Ni—03/OT). The reaction was carried out at 185° and 800 psi $H_2$ pressure during 7 hrs. The product recovered weighed 45.3 g. Dimethylformamide was added as an internal standard and the assay carried out as in Example 1. The ratio of THF to 1,4-BAD in the product was 0.97.

EXAMPLE 9

The charge of Example 1 was used, replacing the Ni-Cu-Cr catalyst by 1.0 g of a Ni-on-kieselguhr catalyst containing 54.6% Ni (Girdler T 1567 RS) and the reduction carried out at 180° and 750 psi $H_2$ during 7 hrs. Product recovery was 44.4 g and the ratio of THF to 1,4-BAD in the product was 1.04. A 42.5% THF and 40.77% 1,4-BAD yield was obtained.

EXAMPLE 10

The vessel of Example 1 was charged with 23 g furan, 20 g of 1 N-NaOH solution, 2.4 g adipic acid, and 1.0 g of the Ni-Cu-Cr catalyst used in Example 1. Approximately 60% of the carboxyl groups of the acid catalyst were neutralized to give a solution of pH 5.0. The hydrogenation was carried out at 180° and 750 psi during 13 hrs. The product weighed 44.395 g. Assay by gas-liquid chromatography showed 37.2% yield of THF and 58.1% of 1,4-BAD or a ratio of 0.64.

EXAMPLE 11

The vessel of Example 1 was charged as in Example 1, replacing the adipic acid by 0.98 g of maleic anhydride. Hydrogenation was complete in 6.5 hrs at 180° and 800 psi $H_2$. Product recovery was 42.9 g. For analysis, 4.765 g of 1,5-pentanediol was added as an internal standard. The yield of THF was 42.6%, of 1,4-BAD, 45.7%, or a ratio of 0.93. Distillation of the product left 2.03 g nonvolatile esters of 1,4-BAD.

EXAMPLE 12

The distillation residue from Example 11 was charged with 20 g furan, 10 g of water (a water/furan ratio of 1.89), 10 g dioxane as an internal standard and 1 g of the catalyst of Example 1. The hydrogenation was carried out for 3 hrs at 180° and 800 psi $H_2$. The product weighed 40.74 g. Assay of the product showed a yield of 59.5% THF and 35.1% 1,4-BAD or a ratio of THF/1,4-BAD of 1.7.

EXAMPLE 13

The process of Example 12 was repeated using the distillation residue from Example 7 (2.2 g), 1 g of the Ni-Cu-Cr catalyst of Example 1 with 20 g furan, 10 g dioxane and 25 g $H_2O$ (a water/furan ratio of 4.72). The hydrogenation required 4½ hrs and product recovered weighed 56.75 g. Assay showed a yield of 42.1% THF and 58.5% 1,4-BAD or a ratio of 0.72. Thus, under comparable conditions the product ratio may be altered by altering the water content of the system.

EXAMPLE 14

The reaction vessel of Example 1 was charged with 20 g furan, 20 g water, 10 g dioxane, 1.95 g succinic acid and 1 g of a 54.6% Ni-on-Kieselguhr catalyst. The reaction was carried out at 160° and 600 psi $H_2$ during 5½ hrs. The yield of THF was 45.6% and of 1,4-BAD 41.1% or a ratio of THF/1,4-BAD of 1.1.

EXAMPLE 15

The vessel of Example 1 was charged with 20 g furan, 20 g water, 10 g dioxane, 1 g of the Ni-Cu-Cr catalyst of Example 1 and 3.4 g sebacic acid. Reduction was carried out at 180° and 800 psi $H_2$ during 5½ hours. The product weighed 57.39 g and assayed for 52.83% THF and 45.42% 1,4-BAD.

I claim:
1. The process of making 1,4-butanediol by contacting furan, water and hydrogen at a temperature in the range of 150°–190° C. under a hydrogen pressure of 500–900 pounds per square inch in the presence of a nonpyrophoric nickel hydrogenation catalyst and an aliphatic dicarboxylic acid or anhydride of 4 to 10 carbon atoms or a derivative thereof having one free carboxylic group, the water/furan molar ratio being at least 2.5 and the amount of said dicarboxylic acid or derivative being at least 1.6 equivalents per liter of combined volume of water and furan.

2. The process of claim 1 carried out at a hydrogen pressure of 600–800 pounds per square inch.

3. The process of claim 1 wherein the nickel catalyst contains about 2–35% by weight of copper based on the nickel content.

4. The process of claim 1 wherein the catalyst is supported.

5. The process of claim 1 wherein the catalyst is nickel supported on alumina.

6. The process of claim 1 wherein the catalyst is nickel supported on kieselguhr.

7. The process of claim 1 wherein the catalyst is nickel and copper supported on alumina.

8. The process of claim 7 wherein the catalyst contains by weight about 47% of nickel and about 16% of copper.

9. The process of claim 1 wherein the catalyst contains nickel and the dicarboxylic acid compound is adipic acid.

10. The process of claim 9 wherein the dicarboxylic acid compound is glutaric acid.

11. The process of claim 9 wherein the dicarboxylic acid compound is succinic acid.

12. The process of claim 9 wherein the dicarboxylic acid compound is maleic anhydride.

13. The process of claim 9 wherein the dicarboxylic acid compound is sebacic acid.

* * * * *